US00PP33667P2

(12) United States Plant Patent
Smith

(10) Patent No.: US PP33,667 P2
(45) Date of Patent: Nov. 23, 2021

(54) ***CHRYSANTHEMUM* PLANT NAMED 'CIFZ0088'**

(50) Latin Name: ***Chrysanthemum* x *morifolium***
Varietal Denomination: CIFZ0088

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/232,349

(22) Filed: Apr. 16, 2021

(51) Int. Cl.
*A01H 5/02* (2018.01)
*A01H 6/14* (2018.01)

(52) U.S. Cl.
USPC ..... Plt./291

(58) Field of Classification Search
USPC ..... Plt./286, 287, 291
See application file for complete search history.

*Primary Examiner* — Susan McCormick Ewoldt
(74) *Attorney, Agent, or Firm* — Dale Skalla

(57) ABSTRACT

A new garden type *Chrysanthemum* plant named 'CIFZ0088' particularly distinguished by its medium size plant with mound plant habit, a medium size decorative flower, pink/lavender flower color with darker flower center and a natural season response late September/early October.

1 Drawing Sheet

Latin name of the genus and species of the plant claimed: *Chrysanthemum* x *morifolium*.
Varietal denomination: 'CIFZ0088'.

BACKGROUND OF THE NEW PLANT

The present invention comprises a new *Chrysanthemum*, botanically known as *Chrysanthemum* x *morifolium*, and hereinafter referred to by the variety name 'CIFZ0088'.

'CIFZ0088' is a product of a planned breeding program. The new cultivar has medium size plant with mound plant habit, a medium size decorative flower, pink/lavender flower color with darker flower center and a natural season response late September/early October.

'CIFZ0088' originated from a natural mutation of 'Regal Yocheryl' in 2017. 'CIFZ0088' was selected from stock that had been flowered to prove the mutation was stable on Jan. 2, 2018 in Alva, Fla.

The female parent was the variety 'Regal Yocheryl', U.S. Plant Pat. No. 13,974.

TABLE 1

Characteristics of the female parent, compared to 'CIFZ0088':

| Trait | 'CIFZ0088' | 'Regal Yocheryl', U.S. Plant Pat. No. 13,974 |
|---|---|---|
| Natural response: | Similar | Similar |
| Blackcloth response: | Similar | Similar |
| Flower size: | Similar | Similar |
| Flower color: | Lighter, two-tone effect more obvious | Darker, two-tone effect less obvious |
| Flower type: | Similar | Similar |
| Plant size: | Less Spread | More Spread |
| Plant habit: | Similar | Similar |

As the new variety is the result of mutation breeding, there is not a male parent.

The first act of asexual reproduction of 'CIFZ0088' was accomplished when vegetative stem cuttings were propagated from the initial selection in January 2018 in Mebane, N.C.

BRIEF SUMMARY OF INVENTION

Horticultural examination of plants grown from cuttings of the plant initiated in January 2018 and continuing thereafter, has demonstrated that the combination of characteristics as herein disclosed for 'CIFZ0088' are firmly fixed and are retained through successive generations of asexual reproduction.

'CIFZ0088' has not been observed under all possible environmental conditions. The phenotype may vary significantly with variations in environment such as temperature, light intensity and day length.

A Plant Breeder's Right for this cultivar has not yet been applied for. 'CIFZ0088' has not been made publicly available prior to the effective filing date of this application, notwithstanding any disclosure that may have been made less than one year prior to the effective filing date of this application by the inventor or another who obtained 'CIFZ0088' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0088' with colors being as true as possible with an illustration of this type.

Figure 1:
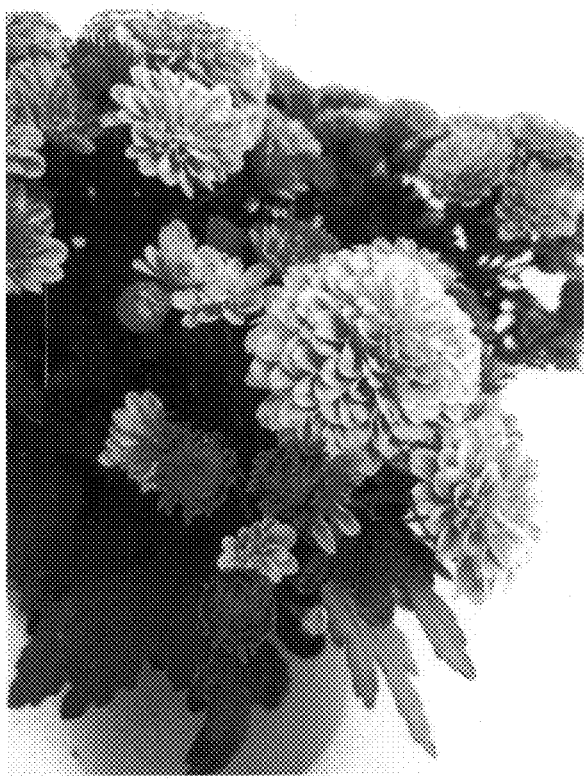
Figure 2:
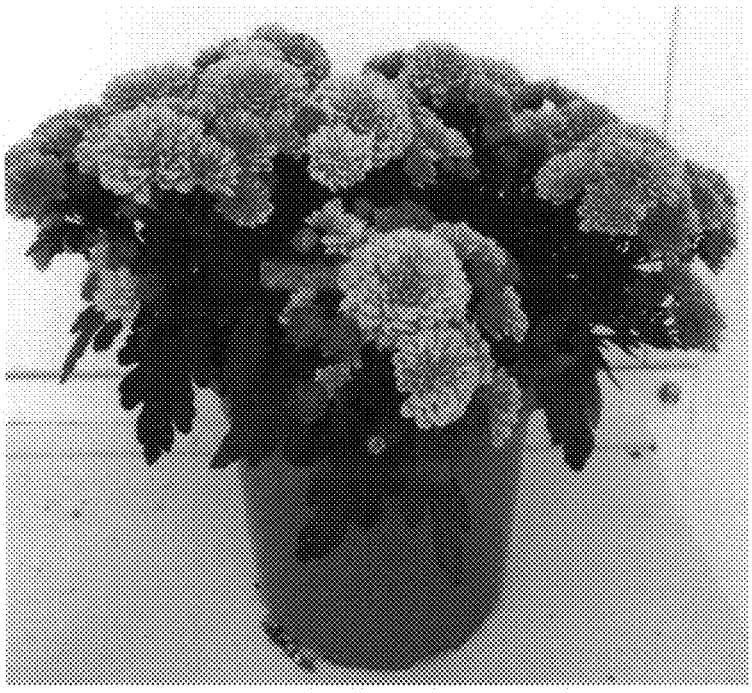

The photographic drawing shows in FIG. 1 a close view of flower of the new variety and in FIG. 2 a flowering plant from an outdoor trial.

The aforementioned photographs: FIG. 1, as well as FIG. 2 were taken in September 2020 both showing a plant from the same blackcloth outdoor trial in Enkhuizen, The Netherlands.

These plants were about 12 weeks of age. One rooted cutting per pot had been planted in a 19 cm pot, not pinched in week 24, and black clothed from week 29. Plants started flowering the end of August.

DETAILED BOTANICAL DESCRIPTION

The measurements were taken in Enkhuizen, The Netherlands in September 2020 on the plants from the aforementioned trial.

Color references are made to The Royal Horticultural Society Colour Chart (R.H.S.) 2001

TABLE 2

DIFFERENCES BETWEEN THE NEW VARIETY 'CIFZ0088' AND TWO MOST SIMILAR VARIETIES:

| Trait | 'CIFZ0088' | 'Yocheryl', U.S. Plant Pat. No. 11,846 |
|---|---|---|
| Natural response: | 1/4 week faster | 1/4 week slower |
| Blackcloth response: | Similar | Similar |
| Flower size: | Similar or bit smaller | Similar or bit larger |
| Flower color: | Similar or bit lighter | Similar or a bit darker |
| Flower type: | Similar | Similar |
| Plant size: | Smaller | Larger |
| Plant habit: | Less height gives more rounded appearance | More height gives more upright appearance |
| Flower longevity: | Similar | Similar |
| Plant strength: | Similar | Similar |
| Flowering uniformity: | Similar | Similar |

TABLE 3

| Trait | 'CIFZ0088' | 'PPP Mil PK05', U.S. Plant Pat. No. 16,968 |
|---|---|---|
| Natural response: | 1/2 week faster | 1/2 week slower |
| Blackcloth response: | At least 1 week faster | At least 1 week slower |
| Flower size: | Smaller | Larger |
| Flower color: | Darker | Lighter |
| Flower type: | Similar | Similar |
| Plant size: | Taller, less spread | Shorter, wider |
| Plant habit: | More even height to width | Flatter/wider |
| Flower longevity: | 40% longer | 40% shorter |
| Flowering uniformity: | More uniform flowering | Less uniform flowering |

Plant:

*Form, growth and habit.*—Herbaceous garden-type, stems Upright and outwardly spreading, freely branching, strong and moderately vigorous growth habit.

*Plant height (above soil).*—11 cm.

*Plant height (inflorescence included).*—17 cm.

*Plant width.*—27 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 147A.

*Immature leaf, color lower surface.*—RHS 147B.

*Mature leaf, color, upper surface.*—RHS 147A.

*Mature leaf, color lower surface.*—RHS 147A.

*Length.*—5.2 cm.

*Width.*—4.1 cm.

*Shape.*—Ovate, with distinct lobes.

*Base shape.*—Attenuate.

*Apex shape.*—Mucronate.

*Margin.*—5-lobed (palmate), edge dentate.

*Number of margin indentations.*—Many.

*Depth of margin indentations.*—Medium.

*Leaf length terminal lobe relative to total leaf length.*—Long.

*Leaf depth lower lateral sinus.*—Medium.

*Texture, upper surface.*—Smooth.

*Texture, lower surface.*—Bifid hairs.

*Color of veins, upper surface.*—RHS 147B.

*Color of veins, lower surface.*—RHS 147B.

*Pattern of veining.*—Palmate.

*Petiole color.*—RHS 147B.

*Petiole length.*—0.9 cm.

*Diameter.*—0.2 cm.

*Texture.*—Bifid hairs.

*Presence of stipules.*—Yes.

*If present, size of stipules.*—Medium.

Stem:

*Quantity of main branches per plant.*—6-8.

*Color of stem.*—RHS 138A.

*Length of stem.*—9.0-10.0 cm.

*Diameter.*—0.5 cm.

*Length of internodes.*—1.5-2.6 cm.

*Texture.*—Bifid hairs.

*Color of peduncle.*—RHS 137C.

*Length of peduncle.*—3.6-4.6 cm.

*Peduncle diameter.*—0.2 cm.

*Texture.*—Bifid hairs.

Inflorescence:

*Type.*—Compositae, solitary, decorative-type inflorescences borne terminally above foliage, ligulate ray florets arranged acropetally on a capitulum giving a double flower.

*Quantity of short days to flowering (response time).*—Approximately 7 weeks.

*Natural season flowering.*—Late September to early October.

*Quantity of inflorescences per plant.*—100-120 with many small buds developing.

*Lastingness of individual blooms on the plant.*—About six weeks from first color.

*Fragrance.*—Spicy.

Bud (when showing color):

*Color.*—RHS 64A.

*Length.*—1.0 cm.

*Width.*—1.1-1.2 cm.

*Shape.*—Ovate.

Immature inflorescence (at moment of opening):

*Diameter.*—2.1-2.5 cm.

*Color of ray florets, upper surface.*—RHS N74D.

*Color of ray florets, lower surface.*—RHS 75A.

Mature inflorescence:

*Diameter.*—4.8 cm.

*Depth.*—2.4 cm.

*Total diameter of disc.*—No disc present.

*Receptacle color.*—RHS 137B.

*Receptacle height.*—0.4 cm.

*Receptacle diameter.*—1.6 cm.

*Length of corolla tube.*—Short.

Ray florets:

*Average quantity of florets.*—170-180 in several whorls.

*Color of florets, upper surface.*—RHS 75B.

*Color lower surface.*—RHS 75B; RHS 75D towards base.

*Length.*—1.9 cm.

*Width/diameter.*—0.7 cm.

*Shape.*—Elliptical.

*Apex shape.*—Obtuse; occasionally dentate.

*Base shape.*—Tube.

*Margin.*—Entire. Small incisions may be present at tip.

*Margin.*—Type of rolling — Moderately involute.

*Texture, upper surface.*—Papillate.

*Lower surface.*—Papillate.

*Ribs present.*—Yes.

*Number of keels.*—2.

*Profile at widest point.*—Weakly convex.

*Longitudional axis shape.*—Reflexing.

Disc florets:

*Number of disc florets.*—No development of disc florets.

Inflorescence (at moment of senescence):

*Color of ray florets, upper surface.*—RHS 75C.

*Color of ray florets, lower surface.*—RHS 75D.

Phyllaries:

*Quantity.*—20-25.

*Color, upper surface.*—RHS 137B.

*Color, lower surface.*—RHS 137B.

*Length.*—0.6 cm.

*Width.*—0.2 cm.

*Shape.*—Lanceolate.

*Apex shape.*—Acute.

*Base.*—Fused.

*Margins.*—Entire.

*Texture, upper surface.*—Glabrous.

*Texture, lower surface.*—Canescent.

Reproductive organs:

*Pistil.*—One.

*Length.*—0.4 cm.

*Style color.*—RHS 150C.

*Style length.*—0.3 cm.

*Stigma color.*—RHS 9B.

*Stigma shape.*—Bi-parted.

*Ovary color.*—RHS 149A.

*Ovary length.*—0.2 cm.

*Ovary width.*—0.1 cm.

Androecium: No disc florets developed and no androecium developed.

*Disease/pest resistance.*—Has not been determined to date.

*Hardiness.*—Has not been determined to date.

What is claimed is:

1. A new and distinct variety of *Chrysanthemum* plant named 'CIFZ0088' substantially as illustrated and described herein.

* * * * *